United States Patent
Gotou et al.

(10) Patent No.: US 7,812,056 B2
(45) Date of Patent: *Oct. 12, 2010

(54) FINE PARTICLE DISPERANT AND COSMETIC, PAINT, INK, MEMORIZING MATERIAL AND LUBRICANT CONTAINING THE DISPERSANT

(75) Inventors: Naoki Gotou, Yokohama (JP); Taro Ehara, Yokohama (JP); Hisanori Kachi, Yokohama (JP); Yoshiaki Iwamoto, Yokohama (JP)

(73) Assignee: The Nisshi OilliO Group, Ltd., Chuo-ku, Tokyo (JP)

( * ) Notice: Subject to any disclaimer, the term of this patent is extended or adjusted under 35 U.S.C. 154(b) by 1410 days.

This patent is subject to a terminal disclaimer.

(21) Appl. No.: 10/950,651

(22) Filed: Sep. 28, 2004

(65) Prior Publication Data

US 2005/0042181 A1    Feb. 24, 2005

Related U.S. Application Data

(63) Continuation of application No. PCT/JP03/03818, filed on Mar. 27, 2003.

(30) Foreign Application Priority Data

Mar. 28, 2002    (JP)    ............................. 2002-092185

(51) Int. Cl.
*A61K 31/20* (2006.01)
*A61K 31/21* (2006.01)
*A61K 31/215* (2006.01)

(52) U.S. Cl. .................. 514/574; 514/558; 424/401; 424/59; 424/63; 424/64

(58) Field of Classification Search .............. 424/401, 424/59, 63, 64; 524/522, 523, 574, 558
See application file for complete search history.

(56) References Cited

U.S. PATENT DOCUMENTS

| | | | | |
|---|---|---|---|---|
| 4,389,346 | A | * | 6/1983 | Yamada et al. ............... 424/63 |
| 5,436,006 | A | * | 7/1995 | Hirose et al. ............... 424/401 |
| 5,468,802 | A | * | 11/1995 | Wilt et al. .................. 524/539 |
| H1536 | H | * | 6/1996 | Karn et al. .................. 508/399 |
| 6,160,144 | A | | 12/2000 | Bongardt et al. |
| 6,214,329 | B1 | * | 4/2001 | Brieva et al. ............... 424/70.7 |
| 6,316,119 | B1 | * | 11/2001 | Metzger et al. ............. 428/520 |
| 6,329,060 | B1 | | 12/2001 | Barkac et al. |
| 6,613,135 | B1 | * | 9/2003 | Miyamoto et al. ....... 106/31.35 |

FOREIGN PATENT DOCUMENTS

| | | |
|---|---|---|
| GB | 1525392 | 9/1978 |
| GB | 2142837 A | 1/1985 |
| JP | 51-118843 A | 10/1976 |
| JP | 52-131513 A | 11/1977 |
| JP | 53-46890 | 12/1978 |
| JP | 53-46890 B2 | 12/1978 |
| JP | 07-034084 A | 2/1995 |
| JP | 08176587 A * | 9/1996 |
| JP | 09053005 A * | 2/1997 |
| JP | 2000-26879 A | 1/2000 |
| JP | 2001-247844 A | 9/2001 |
| JP | 2001-247845 A | 9/2001 |
| JP | 2001-288006 A | 10/2001 |
| JP | 63-125598 A | 5/2008 |

OTHER PUBLICATIONS

Akagi, N., Feb. 25, 1997, Derwent Acc. No. 1997-197343, (JP 09053005, Abstract).*
Ishii, K. et al."Perfume Composition", JP 408176587 A, abstract.*

* cited by examiner

*Primary Examiner*—Gina C Yu
(74) *Attorney, Agent, or Firm*—Buchanan Ingersoll & Rooney PC

(57) ABSTRACT

A fine particle dispersant containing at least one member selected from the group consisting of ester compounds of the following general formula (I) of ditrimethylolpropane and a fatty acid(s), polycondensates of ditrimethylolpropane and a polyvalent carboxylic acid(s), polycondensates of the ester compound of the following general formula (I) and the polyvalent carboxylic acid(s), polycondensates of an ester compound of ditrimethylolpropane and the polyvalent carboxylic acid(s) and the fatty acid(s), and polycondensates of ditrimethylolpropane, the fatty acid(s) and the polyvalent carboxylic acid(s).

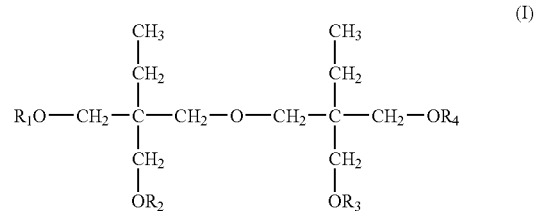

wherein $R_1$ to $R_4$ each independently represent a hydrogen atom or a fatty acid residue, with the proviso that at least one of them is a hydrogen atom. This fine particle dispersant is excellent in fine particle dispersibility and the properties (smell and color) thereof are scarcely deteriorated in heat stability tests.

6 Claims, No Drawings

FINE PARTICLE DISPERANT AND COSMETIC, PAINT, INK, MEMORIZING MATERIAL AND LUBRICANT CONTAINING THE DISPERSANT

BACKGROUND OF THE INVENTION

The present invention relates to a fine particle dispersant as well as cosmetics, paints, inks, memorizing materials and lubricants containing the dispersant.

Techniques for dispersing fine particles are now employed in various fields of cosmetics, paints, inks, memorizing materials, lubricants, medicines, foods, etc. Main factors for determining the fine particle-dispersing function are, for example, characteristics of the fine particles such as pigments and also characteristics of vehicles such as resins, solvents and additives. Particularly for the latter, various ideas were proposed for improving the fine particle-dispersing function in various fields.

In the field of cosmetics, for example, castor oil has so far been used as base oil for a lipstick for dispersing a pigment. Because ricinoleic acid which is a typical hydroxyl acid is a main fatty acid component of castor oil, this oil has a polarity higher than that of other vegetable oils, hydrophilic property, humectant effect and a high viscosity. Taking advantage of these properties, ricinoleic acid has been used as a medium in kneading a pigment from old times. Castor oil is usually used in an amount of 20 to 50% based on a liquid oil in the base. If castor oil is used in an excessive amount, problems such as an odor of the castor oil and deterioration of feeling upon use thereof with time are posed. In addition, because castor oil has a high polarity, the compatibility thereof with a starting hydrocarbon is low and, therefor, the use of an ester oil as a binder is indispensable. Another problem of castor oil is that it is irritating.

Japanese Patent Examined Publication (hereinafter referred to as "J. P. KOKOKU") No. Sho 53-46890/1978 discloses cosmetics containing a full ester compound of trimethylolpropane. It is described therein that basic cosmetics, makeup cosmetics, hair cosmetics, etc. having an excellent feel to the touch to the skin and also excellent storability can be provided. Japanese Patent Unexamined Published Application (hereinafter referred to as "J. P. KOKAI") Nos. 247844/2001 and 247845/2001 disclose a gelling agent comprising an esterification product obtained by the esterification reaction of trimethylolpropane or its condensate, a glycerol condensate, a long-chain, linear saturated basic acid having 6 to 30 carbon atoms and a fatty acid having 8 to 28 carbon atoms.

However, those specifications are silent about a fine particle dispersant having an excellent fine particle-dispersibility and only a slight deterioration of the properties (odor and color) in heat stability tests.

DISCLOSURE OF THE INVENTION

The object of the present invention is to provide a fine particle dispersant excellent in the fine particle dispersibility and having only slight deterioration in the properties (odor and color) in heat stability tests.

Another object of the present invention is to provide cosmetics, paints, inks, memorizing materials and lubricants containing the fine particle dispersant.

The present invention has been completed on the basis of findings that a partially esterified compound from a ditrimethylolpropane and a fatty acid(s), and a polycondensate of the ester compound and a polyvalent carboxylic acid(s) have an excellent effect as fine particle dispersants and that the above-described problems can be efficiently solved with them.

Namely, the present invention provides a fine particle dispersant containing at least one member selected from the group consisting of ester compounds of the following general formula (I) obtained from ditrimethylolpropane and a fatty acid(s), polycondensates of ditrimethylolpropane and a polyvalent carboxylic acid(s), polycondensates of the ester compound of the following general formula (I) and the polyvalent carboxylic acid(s), polycondensates of an ester compound of ditrimethylolpropane and the polyvalent carboxylic acid(s) and the fatty acid(s), and polycondensates of ditrimethylolpropane, the fatty acid(s) and the polyvalent carboxylic acid(s).

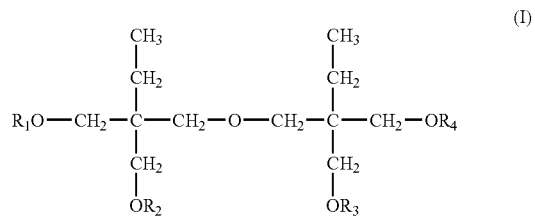

wherein $R_1$ to $R_4$ each independently represent a hydrogen atom or a fatty acid residue, with the proviso that at least one of them is a hydrogen atom.

The present invention also provides cosmetic compositions, paint compositions, ink compositions, memorizing materials and lubricant compositions containing the fine particle dispersant.

BEST MODE FOR CARRYING OUT THE PRESENT INVENTION

The fatty acids for forming the ester compounds of general formula (I) used in the present invention are preferably linear or branched fatty acids (namely aliphatic monocarboxylic acids) having 5 to 28 carbon atoms (preferably 6 to 28 carbon atoms). Fatty acids having a branch are particularly preferred. The fatty acids having a branch include, for example, pivalic acid, isoheptanoic acid, 4-ethylpentanoic acid, isooctylic acid, 2-ethylhexanoic acid, 4,5-dimethylhexanoic acid, 4-propylpentanoic acid, isononylic acid (isononanoic acid), 2-ethylheptanoic acid, 3,5,5-trimethylhexanoic acid, isodecanoic acid, isododecanoic acid, 2-methyldecanoic acid, 3-methyldecanoic acid, 4-methyldecanoic acid, 5-methyldecanoic acid, 6-methyldecanoic acid, 7-methyldecanoic acid, 9-methyldecanoic acid, 6-ethylnonanoic acid, 5-propyloctanoic acid, isolauric acid, 3-methylhendecanoic acid, 6-propylnonanoic acid, isotridecanoic acid, 2-methyldodecanoic acid, 3-methyldodecanoic acid, 4-methyldodecanoic acid, 5-methyldodecanoic acid, 11-methyldodecanoic acid, 7-propyldecanoic acid, isomyristic acid, 2-methyltridecanoic acid, 12-methyltridecanoic acid, isopalmitic acid, 2-hexyldecanoic acid, 14-methylpentadecanoic acid, 2-ethyltetradecanoic acid, isostearic acid, methyl-branched isostearic acid, 2-heptylundecanoic acid, 2-isoheptylisoundecanoic acid, 2-ethylhexadecanoic acid, 14-ethylhexadecanoic acid, 14-methylheptadecanoic acid, 15-methylheptadecanoic acid, 16-methylheptadecanoic acid, 2-butyltetradecanoic acid, isoarachic acid, 3-methylnonadecanoic acid, 2-ethyloctadecanoic acid, isohexacosanoic acid, 24-methylheptacosanoic acid, 2-ethyltetracosanoic acid, 2-butyldocosanoic acid, 2-hexylicosanoic acid, 2-octyloctadecanoic acid and 2-decylhexadecanoic acid. Those fatty acids are usable either alone or in the form of a mixture of them. In them, fatty acids having 8 to 18 are preferred. Particularly preferred branched fatty acids having 8 to 18 carbon atoms are, for example, isooctylic acids (preferably 2-ethylhexanoic acid and 4,5-dimethylhexanoic acid), isononanoic acids (preferably 2-ethylheptanoic acid and 3,5,5-trimethylhexanoic acid), isotridecanoic acid, isopalmitic acid and isostearic acids (preferably methyl-branched isostearic acid, 2-heptylundecanoic acid and 2-isoheptylisoundecanoic acid). Branched saturated fatty acids having 8 to 18 carbon atoms (branched saturated aliphatic monocarboxylic acids) such as isooctylic acid, isononylic acid (isononanoic acid), isotridecanoic acid and isostearic acid are particularly preferred.

The linear fatty acids are those having 6 to 28 carbon atoms. They include saturated fatty acids such as caproic acid, caprylic acid, octylic acid, nonylic acid, decanoic acid, dodecanoic acid, lauric acid, tridecanoic acid, myristic acid, palmitic acid, stearic acid and behenic acid; and unsaturated fatty acids such as caproleic acid, undecylenic acid, myristoleic acid, palmitoleic acid, oleic acid, elaidic acid, gondoic acid and erucic acid. They can be used either alone or in the form of a mixture of two or more of them.

The ester compounds in the present invention are mono-, di-, tri- and tetra-ester compounds as well as mixtures of two or more of them. The ester compounds may also be a mixture of one or more of these partial esters and the tetra-ester.

The polyvalent carboxylic acids used for preparing the polycondensates in the present invention are preferably dibasic carboxylic acids having 2 to 10 carbon atoms such as succinic acid, adipic acid, azelaic acid and sebacic acid. Dibasic saturated carboxylic acids having 6 to 10 carbon atoms are particularly preferred. They are usable either alone or in the form of a mixture of two or more of them.

In the present invention, it is also preferred to use a mixture of a branched fatty acid having 8 to 18 carbon atoms (a branched aliphatic monocarboxylic acid, preferably a branched saturated aliphatic monocarboxylic acid) and a dibasic carboxylic acid having 2 to 10 carbon atoms (in particular a dibasic saturated carboxylic acid having 6 to 10 carbon atoms). In this case, the branched saturated fatty acid and the dibasic carboxylic acid are preferably used in a molar ratio of 70/30 to 95/5.

The ester compounds and polycondensates in the present invention are preferably those having a hydroxyl value (OHV) of 10 to 150, more preferably those having a hydroxyl value of 30 to 150 and most preferably those having a hydroxyl value of 40 to 100. When OHV is in the above-described range, the wetting of the fine particle surface is improved, the compatibility with a polar oil is improved and the excellent effect of the particle dispersant can be exhibited. OHV indicates the amount (mg) of potassium hydroxide required for neutralizing acetic acid necessitated for acetylating free OH group in 1 gram of the sample. The ester compounds of general formula (I) and the polycondensates thereof are preferably in liquid form at room temperature or, in other words, they preferably have a viscosity (25° C.) of 100 to 30,000 mPa·s.

The ester compounds and polycondensates thereof in the present invention can be obtained by, for example, the esterification and/or dehydration condensation reaction of 1 equivalent of ditrimethylolpropane and 1.5 to 3.5 equivalents of a fatty acid and/or polyvalent carboxylic acid in the absence of catalyst or in the presence of a catalyst (such as tin chloride) at 180 to 240° C. After the completion of the reaction, the reaction mixture is subjected to an adsorption treatment or the like to remove the catalyst and then low-molecular substances such as the unreacted starting materials are removed by the distillation or the like to obtain the intended product.

The fine particles which can be dispersed with the ester compounds and polycondensates thereof in the present invention are various particles having a size of several nm to several μm, preferably 10 nm to 1 μm, particularly colloidal particles. Examples of them include inorganic pigments such as zinc oxide, titanium oxides, iron oxides, mica, ultramarine, carbon black, clay, kaolin and talc; organic pigments such as Red No. 202, Red No. 226, Blue No. 1, Blue No. 404, Yellow No. 4 and Yellow No. 205; magnetic particles such as $\gamma$-$Fe_2O_3$, Co-$\gamma$-$Fe_2O_3$, and $CrO_2$; and solid lubricants such as $MoS_2$ and graphite.

The ester compounds and polycondensates thereof in the present invention may be suitably added to the above-described fine particle-containing cosmetics, paints, inks, memorizing materials, lubricants, etc.

For example, when the ester compound or polycondensate thereof is to be added to a cosmetic, ½ to 3 parts by weight (preferably 1 to 2 parts by weight) of the fine particle dispersant of the present invention is added to 0.1 to 50 parts (preferably 1 to 30 parts) of titanium oxide, Red NO. 202, iron oxide red or mica which is ordinarily used as a starting material for cosmetics, they are kneaded together to previously prepare a concentrated dispersant, 10 to 90% of the concentrated dispersant is incorporated into various cosmetics to form a dispersion cosmetic. In this case, the fine particle dispersant of the present invention is also usable as a base oil for the cosmetic.

When the ester compound or polycondensate thereof is to be added to a paint, ½ to 3 parts by weight (preferably 1 to 2 parts by weight) of the fine particle dispersant of the present invention is added to 0.1 to 30 parts (preferably 5 to 20 parts) of a pigment such as carbon black, Phthalocyanine Blue, Phthalocyanine Green, yellow oxide of iron, red oxide of iron or zinc oxide, and they are kneaded together. After the pigment surface has been sufficiently wetted, about 10 to 90% of the concentrated dispersant is added to the paint composition to obtain a coloring paint of pigment dispersion type.

When the fine particle dispersant of the present invention is to be incorporated into an ink, ½ to 3 parts by weight (preferably 1 to 2 parts by weight) of the fine particle dispersant is added to 0.1 to 30 parts (preferably 5 to 20 parts) of a pigment such as carbon black, titanium oxide, Phthalocyanine Blue, Disazo Yellow, Carmine 6B or Lake Red C, and they are kneaded together. After the pigment surface has been sufficiently wetted, about 10 to 90% of the concentrated dispersant is added to the ink composition to obtain an ink of pigment dispersion type.

When the fine particle dispersant of the present invention is to be incorporated into a magnetic memorizing material, ½ to 3 parts by weight (preferably 1 to 2 parts by weight) of the fine particle dispersant is added to 0.1 to 20 parts (preferably 5 to 10 parts) of magnetic particles such as $\gamma$-$Fe_2O_3$ or $CrO_2$, and they are kneaded together. After the magnetic particles have been sufficiently wetted, about 10 to 30% of the concentrated dispersant is added to the magnetizing ink composition to obtain a magnetic paint of dispersion type.

When the fine particle dispersant of the present invention is to be incorporated into a lubricant, ½ to 3 parts by weight (preferably 1 to 2 parts by weight) of the fine particle dispersant is added to 0.1 to 15 parts (preferably 1 to 10 parts) of a solid lubricant such as graphite, molybdenum disulfide or PTFE, and they are kneaded together. After the solid lubricant has been sufficiently wetted, about 1 to 30% of the concentrated dispersant is added to the mineral or synthetic lubricating oil (or a mixture of a mineral oil and a synthetic oil) or grease to obtain a lubricant of a solid lubricant dispersion type.

The fine particle pigment is used for the following purposes particularly in the field of cosmetics:
(1) Liver spots, freckles, etc. are suitably covered up with a film of the pigment.
(2) The fine particle pigment corrects the skin color to a natural, healthy complexion.
(3) The fine particle pigment tints the skin to a desired color to make the skin attractive.
(4) The fine particle pigment cut ultraviolet rays to protect the skin from a sunburn.
(5) The fine particle pigment absorbs sweat, sebum, etc. secreted through the skin to prevent the face from being greasy.

Thus, improvement in the quality of cosmetics by improving the dispersibility by using the fine particle dispersant of the present invention can be expected in skin care cosmetics (particularly preferably sunscreens, packs, etc.) and makeup cosmetics (particularly preferably lipsticks, lip creams, foundations, cheek rouges, eye shadows, eye liners, eyebrows, mascaras and manicures). It is expected that by formulating the composition of cosmetics with additives which will be described below, the cosmetics quite excellent in the properties and stability can be provided.

If necessary, various ordinary components can be incorporated into the cosmetics of the present invention, so far as the effects of the present invention are not damaged, to obtain the intended product by an ordinary method. The cosmetics can be obtained by an ordinary method which varies depending on the intended dosage form by suitably incorporating, for example, any of anionic surfactants, cationic surfactants, amphoteric surfactants, lipophilic nonionic surfactants, hydrophilic nonionic surfactants, natural surfactants, liquid oils and fats, solid oils and fats, waxes, hydrocarbon oils, higher fatty acids, higher alcohols, ester oils, silicone oils, powder components, humectants, natural water-soluble high-molecular substances, semi-synthetic water-soluble high-molecular substances, synthetic water-soluble high-molecular substances, inorganic water-soluble high-molecular substances, thickeners, ultraviolet absorbers, sequestering agents, lower alcohols, polyhydric alcohols, monosaccharides, oligosaccharides, polysaccharides, amino acids, organic amines, synthetic resin emulsions, pH regulators, vitamins, antioxidants, antioxidant assistants, perfumes and water. Concrete examples of the components usable for this purpose will be given below.

The anionic surfactants are, for example, basis materials for soap, fatty acid soaps such as sodium laurate and sodium palmitate; higher alkyl sulfates such as sodium lauryl sulfate and potassium lauryl sulfate; alkyl ether sulfuric acid ester salts such as POE-laurylsulfuric acid triethanolamine and POE-sodium laurylsulfate; N-acylsarcosines such as sodium lauroylsarcosine; higher fatty acid amide sulfonates such as sodium N-myristoyl-N-methyltaurine, sodium coconut oil fatty acid methyltauride and sodium laurylmethyltauride; phosphoric ester salts such as sodium POE-oleyl ether phosphate and POE-stearyl ether phosphate; sulfosuccinates such as sodium di-2-ethylhexylsulfosuccinate, sodium monolauroyl-monoethanolamide polyoxyethylenesulfosuccinates and sodium lauryl-polypropylene glycol sulfosuccinate; alkylbenzenesulfonates such as sodium linear dodecylbenzenesulfonate, linear dodecylbenzenesulfonate triethanolamine and linear dodecylbenzenesulfonic acid; N-acylglutamates such as monosodium N-lauroylglutamate, disodium N-stearoylglutamate and monosodium N-myristoyl-L-glutamate; sulfuric ester salts of higher fatty acid esters such as sodium hardened coconut oil fatty acid glycerol sulfate; sulfated oils such as Turkey red oil; POE-alkyl ether carboxylic acids, POE-alkylaryl ether carboxylic acid salts, α-olefin-sulfonic acid salts, higher fatty acid ester sulfonic acid salts, secondary alcohol sulfuric acid esters, higher fatty acid alkylolamide sulfuric acid ester salts, sodium lauroylmonoethanolamide succinate, N-palmitoylaspartic acid ditriethanolamine and sodium caseinate.

The cationic surfactants are, for example, alkyltrimethylammonium salts such as stearyltrimethylammonium chloride and lauryltrimethyl-ammonium chloride; alkylpyridinium salts such as distearyldimethyl-ammonium dialkyldimethylammonium chlorides, poly(N,N'-dimethyl-3,5-methylenepiperidinium) chloride and cetylpyridinium chloride; alkyl quaternary ammonium salts, alkyldimethylbenzylammonium salts, alkylisoquinolinium salts, dialkyl morpholinium salts, POE-alkylamines, alkylamine salts, polyamine fatty acid derivatives, amyl alcohol fatty acid derivatives, benzalkonium chloride and benzethonium chloride.

The amphoteric surfactants are, for example, amphoteric imidazoline surfactants such as sodium 2-undecyl-N,N,N-(hydroxyethylcarboxymethyl)-2-imidazoline and disodium 1-carboxyethyloxy 2-cocoyl-2-imidazolinium hydroxide; 2-heptadecyl-N-carboxymethyl-N-hydroxyethyl-imidazolinium-betaine, lauryldimethylaminoacetic acid-betaine, alkylbetaines, amidobetaines and sulfobetaine.

The lipophilic nonionic surfactants are, for example, sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glycerol/fatty acid esters such as glycerol esters of mono-cotton seed oil fatty acids, glycerol monoerucate, glycerol sesquioleate, glycerol monostearate, glycerol α,α'-oleate pyroglutamate and glycerol monostearate; polyglycerol/fatty acid esters such as diglyceryl monoisostearate and diglyceryl diisostearate; propylene glycol/fatty acid esters such as propylene glycol monostearate, hardened castor oil derivatives and glycerol alkyl ethers.

The hydrophilic nonionic surfactants are, for example, POE-sorbitan/fatty acid esters such as POE-sorbitan monooleate, POE-sorbitan monostearate, POE-sorbitan monooleate and POE-sorbitan tetraoleate; POE-sorbitol/fatty acid esters such as POE-sorbitol monolaurate, POE-sorbitol monooleate, POE-sorbitol pentaoleate and POE-sorbitol monostearate; POE-glycerol/fatty acid esters such as POE-glycerol monostearate, POE-glycerol monoisostearate and POE-glycerol triisostearate; POE-fatty acid esters such as POE-monooleate, POE-distearate, POE-monodioleate and ethylene glycol distearate; POE-alkyl ethers such as POE-lauryl ether, POE-oleyl ether, POE-stearyl ether, POE-behenyl ether, POE-2-octyldodecyl ether and POE-cholestanol ether; Pluronic surfactants such as Pluronic per se; POE•POP-alkyl ethers such as POE POP-cetyl ether, POE POP-2-decyltetradecyl ether, POE•POP-monobutyl ether, POE•POP-hydrogenated lanoline and POE•POP-glycerol ether; tetraPOE•tetraPOP-ethylenediamine condensates such as Tetronic; POE-castor oil-hardened castor oil derivatives such as POE-castor oil, POE-hardened castor oil, POE-hardened castor oil monoisostearate, POE-hardened castor oil triisostearate, POE-hardened castor oil monopyroglutamate monoisostearate diester and POE-hardened castor oil maleate; POE-bees wax lanolin derivatives such as POE-sorbitol bees wax; alkanolamides such as coconut oil fatty acid diethanolamides, lauric acid monoethanolamide and fatty acid isopropanolamides; POE-propylene glycol fatty acid esters, POE-alkylamines, POE-fatty acid amides, sucrose fatty acid esters, POE-nonylphenyl formaldehyde condensate, alkylethoxy-dimethylamine oxides and triolelylphosporic acid.

The natural surfactants are, for example, soybean phospholipids, hydrogenated soybean phospholipids, egg yolk phospholipids and hydrogenated egg yolk phospholipids.

The liquid oils and fats are, for example, avocado oil, camellia oil, turtle oil, macadamia nut oil, corn oil, sunflower oil, mink oil, olive oil, rapeseed oil, egg yolk oil, sesame oil, persic oil, wheat germ oil, sasanqua oil, castor oil, linseed oil, safflower oil, grape seed oil, cotton seed oil, perilla oil, soybean oil, peanut oil, tea fruit oil, kaya oil, rice bran oil, Chinese tung oil, Japanese tung oil, jojoba oil, germ oil, evening primrose oil, glycerol trioctanoate and glycerol tri-isopalmitate.

The solid oils and fats are, for example, cacao butter, coconut oil, beef tallow, mutton tallow, horse fat, palm kernel oil, lard, beef bone fat, Japan wax kernel oil, beef foot fat, Japan wax, hardened coconut oil, hardened palm oil, hardened beef tallow, hardened oil and hardened castor oil.

The waxes are, for example, bees wax, candelilla wax, cotton wax, carnauba wax, bayberry wax, insect wax, spermaceti, montan wax, rice bran wax, kapok wax, sugar cane wax, lanolin, lanolin acetate, liquid lanolin, isopropyl esters of lanolin fatty acids, reduced lanolin, hard lanolin, hexyl laurate, jojoba wax, shellac wax, POE lanolin alcohol ether, POE lanolin alcohol acetate, POE cholesterol ether, lanolin fatty acid polyethylene glycol and POE hydrogenated lanolin alcohol ethers.

The hydrocarbon oils are, for example, liquid paraffin, isoparaffin, paraffin, ozocerite, squalane, pristane, ceresine, squalene, vaseline, microcrystalline wax, paraffin wax and α-olefin oligomers.

The higher fatty acids are, for example, lauric acid, myristic acid, palmitic acid, stearic acid, behenic acid, oleic acid, undecylenic acid, cholic acid, isostearic acid, linoleic acid, linolenic acid, eicosapentaenoic acid (EPA) and docosahexaenoic acid (DHA).

The higher alcohols are, for example, linear alcohols such as lauryl alcohol, cetyl alcohol, stearyl alcohol, behenyl alcohol, myristyl alcohol, oleyl alcohol and cetostearyl alcohol; and branched alcohols such as monostearyl glycerol ether (batyl alcohol), 2-decyltetradecinol, lanoline alcohol, cholesterol, phytosterol, hexyldodecanol, isostearyl alcohol and octyldodecanol.

The ester oils are, for example, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, octyldodecyl lactate, lanolin acetate, isocetyl stearate, isocetyl isostearate, cholesteryl 12-hydroxystearate, ethylene glycol di-2-ethylhexanoate, dipentaerythritol fatty acid esters, N-alkylglycol monoisostearates, neopentyl glycol dicaprate, diisostearyl malate, glycerol di-2-heptylundecanoate, trimethylolprop ane tri-2-ethylhexanoate, trimethylolprop ane triisostearate, pentaerythritol tetra-2-ethylhexanoate, glyceryl tri-2-ethylhexanoate, tri (capryl•caprin•myristin•stearic acid)glyceride, trimethylolpropane triisostearate, cetyl 2-ethylhexanoate, 2-ethylhexyl palmitate, glycerol trimyristate, tri-2-heptylundecanoic acid glyceride, methyl esters of castor oil fatty acids, oleyl oleate, acetoglyceride, 2-heptylundecyl palmitate, diisobutyl adipate, glycerol (adipic acid•2-ethylhexanoic acid•stearic acid) oligoesters, diglyceryl(2-hexyldecanoic acid•sebacic acid) oligoesters, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, Diisopropyl sebacate, 2-ethylhexyl succinate, ethyl acetate, butyl acetate and triethyl citrate.

The silicone oils are, for example, linear polysiloxanes such as dimethyl polysiloxane, methylphenyl polysiloxane and methyl hydrogen polysiloxane; cyclic polysiloxanes such as octamethylcyclotetrasiloxane, decamethylcyclopentasiloxane, dodecamethylcyclohexasiloxane and tetra-hydrotetramethylcyclotetrasiloxane; and polyoxyethylene polyalkylsiloxanes.

The powder components are, for example, inorganic powders such as talc, kaolin, mica, sericite, commonmica, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (calcined gypsum), calcium phosphate, fluorine apatite, hydroxyapatite, ceramic powder, metal soaps (zinc myristate, calcium palmitate and aluminum stearate) and boron nitride; organic powders such as polyamide resin powder (nylon powder), polyethylene powder, polymethyl methacrylate powder, polystyrene powder, styrene/acrylic acid copolymer resin powder, benzoguanamine resin powder, polyethylene tetrafluoride powder and cellulose powder; inorganic white pigments such as titanium dioxide and zinc oxide; inorganic red pigments such as iron oxide (rouge) and iron titanate; inorganic brown pigments such as γ-iron oxide; inorganic yellow pigments such as yellow iron oxide and yellow ochre; inorganic black pigments such as black iron oxide, carbon black and titanium oxide of a low oxidation extent; inorganic violet pigments such as mango violet and cobalt violet; inorganic green pigments such as chromium oxide, chromium hydroxide and cobalt titanate; inorganic blue pigments such as ultramarine and Prussian blue; pearl pigments such as titanium oxide-coated mica, titanium oxide-coated bismuth oxychloride, titanium oxide-coated talc, colored titanium oxide-coated mica, bismuth oxychloride and fish scale flake; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; organic pigments containing zirconium, barium or aluminum lake such as Red No. 3, Red No., 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue NO. 1; and natural pigments such as chlorophyll and β-carotene. Powders are not limited to the above-described materials and those ordinarily incorporated into cosmetics are also usable herein.

The humectants are, for example, polyethylene glycol, propylene glycol, glycerol, 1,3-butylene glycol, xylitol, sorbitol, maltitol, chondroitin sulfate, hyaluronic acid, mucoitin sulfate, charonin sulfate, atero-collagen, cholesteryl-12-hydroxystearate, sodium lactate, urea, bile acid salts, dl-pyrrolidone carboxylates, short chain soluble collagen, diglycerol (EO) PO adducts, hestnut rose extract, yarrow extract and melilotus extract.

The natural water-soluble high-molecular substances are, for example, vegetable high-molecular substances such as acacia, tragacanth gum, galactan, guar gum, Carob gum, Karaya gum, carrageenan, pectin, agar, quince seeds, algae colloid (marine plants extract) and starch (rice, corn, potato and wheat); high-molecular substances from microorganisms such as xantham gum, dextran, succinoglucan and pullulan; and high-molecular substances from animals such as collagen, casein, albumin and gelatin.

The semi-synthetic water-soluble high-molecular substances are, for example, high-molecular starches such as carboxymethyl starch and methylhydroxypropyl starch; high-molecular celluloses such as methylcellulose, nitrocellulose, methylhydroxypropylcellulose, sodium cellulose sulfate, hydroxypropylcellulose, carboxymethylcellulose, sodium cellulose glycolate, crystalline cellulose and cellulose powder; and high-molecular alginates such as sodium alginate and propylene glycol alginate.

The synthetic water-soluble high-molecular substances are, for example, polyvinyl compounds such as polyvinyl alcohol, polyvinyl methyl ether, polyvinylpyrrolidone and carboxyvinyl polymer (Carbopol); polyoxyethylene compounds such as polyethylene glycol 20,000, 40,000, 60,000, etc. and polyoxyethylene polyoxypropylene copolymers; acrylic polymers such as polysodium acrylate, polymethyl acrylate and polyacrylamide; polyethyleneimines and cationic polymers.

The inorganic water-soluble high-molecular substances are, for example, bentonite, AlMg silicate (Veegum), Laponite, hectorite and silicic acid anhydride.

The thickeners are, for example, acacia, carrageenan, Karaya gum, tragacanth gum, Carob gum, quince seeds, casein, dextran, gelatin, sodium pectate, sodium arachate, methylcellulose, ethylcellulose, CMC, hydroxyethylcellulose, hydroxypropylcellulose, PVA, PVM, PVP, polysodium acrylate, carboxyvinyl polymer, locust bean gum, guar gum, tamarind gum, dialkyldimethylammonium sulfate cellulose, xantham gum, aluminum magnesium silicate, bentonite and hectorite.

The ultraviolet absorbers are, for example, benzoic acid ultraviolet absorbers such as p-aminobenzoic acid (hereinafter referred to as PABA), monoglycerol ester of PABA, ethyl ester of N,N-dipropoxyPABA, ethyl ester of N,N-diethoxyPABA, ethyl ester of N,N-dimethylPABA, butyl ester of N,N-dimethylPABA and ethyl ester of N,N-dimethylPABA; anthranilic acid ultraviolet absorbers such as homomenthyl-N-acetylanthranylate; salicylic acid ultraviolet absorbers such as amyl salicylate, menthyl salicylate, homomenthyl salicylate, octyl salicylate, phenyl salicylate, benzyl salicylate and p-isopropanolphenyl salicylate; sinnamic acid ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate and glyceryl mono-2-ethylhexanoyl-di-p aramethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxy-benzophenone, 2-hydroxy-4-methoxy-4'-methylbenzophenone, 2-hydroxy-4-methoxybenzophenone-5-sulonate, 4-phenylbenzophenone, 2-ethylhexyl-4'-phenylbenzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, ethyl urocanate, 2-phenyl-5-methylbenzoxazole, 2,2'-hydroxy-5-methylphenylbenzotriazole, 2-(2'-hydroxy-5'-t-octylphenyl) benzotriazole, 2-(2'-hydroxy-5'-methylphenyl)-benzotriazole, dianisoylmethane, 4-methoxy-4'-t-butyldibenzoylmethane, 5-(3,3-dimethyl-2-norbornylidene)-3-pentan-2-on and 2,4,6-trianilino-p-(carbo-2'-ethylhexyl-1'-oxy)-1,3,5-triazine.

The sequestering agents are, for example, 1-hydroxyethane-1,1-diphosphonic acid, tetrasodium 1-hydroxyethane-1,1-diphosphonate, disodium edetate, trisodium edetate, tetrasodium edetate, sodium citrate, polysodium phosphate, sodium metaphosphate, gluconic acid, phosphoric acid, citric acid, ascorbic acid, succinic acid, edetic acid and trisodium ethylenediaminehydroxyethyltriacetate.

The lower alcohols are, for example, methanol, ethanol, propanol, isopropanol, isobutyl alcohol and t-butyl alcohol.

The polyhydric alcohols are, for example, dihydric alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; trihydric alcohols such as glycerol, trimethylolpropane and 1,2, 6-hexanetriol; tetrahydric alcohols such as pentaerythritol; pentahydric alcohols such as xylitol; hexahydric alcohols such as sorbitol and mannitol; polyhydric alcohol polymers such as diethylene glycol, dipropylene glycol, triethylene glycol, polypropylene glycols, tetraethylene glycol, diglycerol, polyethylene glycols, triglycerol, tetraglycerol and polyglycerols; alkyl ethers of dihydric alcohols such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether; alkyl ethers of dihydric alcohols such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate; glycerol monoalkyl ethers such as chimyl alcohol, oleyl glyceryl ether and batyl alcohol; sugar alcohols such as sorbitol, maltitol, maltotriose, mannitol, sucrose, erythritol, glucose, fructose, starch sugar, maltose, xylitose and alcohols obtained by reducing starch sugar, tetrahydrofurfuryl alcohol, POE-tetrahydrofurfuryl alcohol, POP-butyl ether, POP•POE-butyl ether, tripolyoxypropylene glycerol ethers, POP-glycerol ethers, POP-glycerol ether phosphate and POP•POE-pentane erythritol ether.

The monosaccharides are, for example, trioses such as D-glycerylaldehyde and dihydroxyacetone; tetraoses such as D-erythrose, D-erythrulose, D-threose and erythritol; pentoses such as L-arabinose, D-xylose, L-lyxose, D-arabinose, D-ribose, D-ribulose, D-xylulose and L-xylulose; hexoses such as D-glucose, D-talose, D-psicose, D-galactose, D-fructose, L-galactose, L-mannose and D-tagatose, heptoses such as aldoheptose and Heptose; octoses such as Octose, deoxy sugars such as 2-deoxy-D-ribose, 6-deoxy-L-galactose and 6-deoxy-L-mannos; amino sugars such as D-glucosamine, D-galactosamine, sialic acid, aminouronic acid and muramic acid; and uronic acids such as D-glucuronic acid, D-mannuronic acid, L-guluronic acid, D-galacturonic acid and L-iduronic acid.

The oligosaccharides are, for example, sucrose, Gentianose, umbelliferose, lactose, planteose, Isolyxose, α,α-trehalose, raffinose, Lyxose, stachyose and verbascose.

The polysaccharides are, for example, cellulose, quince seeds, chondroitin sulfate, starch, galactan, dermatan sulfate, glycogen, gum arabic, heparan sulfate, hyaluronic acid, tragacanth gum, keratin sulfate, chondroitin, xantham gum, mucoitin sulfate, guar gum, dextran, keratosulfate, locust bean gum, succinoglucan and charonin acid.

The amino acids are, for example, neutral amino acids such as threonine and cysteine; and basic amino acids such as hydroxylysine. The amino acid derivatives are, for example, sodium acylsarcosines (sodium lauroylsarcosine), acylglutamic acid salts, sodium acyl-β-alanines, glutathione and pyrrolidone carboxylic acids.

The organic amines are, for example, monoethanolamine, diethanolamine, triethanolamine, morpholine, triisopropanolamine, 2-amino-2-methyl-1,3-propanediol and 2-amino-2-methyl-1-propanol.

The synthetic resin emulsions are, for example, acrylic resin emulsions, polyethyl acrylate emulsions, acryl resin emulsions, polyalkyl acrylate emulsions and polyvinyl acetate resin emulsions.

The pH regulators are, for example, buffering agents such as lactic acid/sodium lactate and citric acid/sodium citrate.

The vitamins are, for example, vitamins A, $B_1$, $B_2$, $B_6$, E and derivatives thereof, pantothenic acid and derivatives thereof and biotin.

The antioxidants are, for example, tocopherols, dibutylhydroxytoluene, butylhydroxyanisole and gallic acid esters.

The antioxidant assistants are, for example, phosphoric acid, citric acid, ascorbic acid, maleic acid, malonic acid, succinic acid, fumaric acid, cephalin, hexametaphosphates, phytic acid and ethylenediaminetetraacetic acid.

Other components which can be incorporated into the composition are antiseptics such as ethylparaben and butylparaben; anti-inflammatory agents such as glycyrrhizic acid derivatives, glycyrrhetinic acid derivatives, salicylic acid derivatives, hinokitiol, zinc oxide and allantoin; whitening agents such as the placenta extract and saxifrage extract; extracts of phellodendron, Japanese coptis, lithospermum root, herbaceous peony, Japanese green gentian, birch, sage, loquat, carrot, aloe, mallow, iris, grape, coix seed, sponge gourd, lily, saffron, cnidium, ginger, Saint-John's-wort, ononis spinosa, garlic, cayenne pepper, dried orange peel, ligusticum root and see weeds; activating agents such as royal jelly, photosensitizing dye, cholesterol derivatives and juvenile blood extract; blood circulation improvers such as benzyl nicotinate, β-butoxyethyl nicotinate, capsaicine, zingerone, cantharis tincture, ichthammol, tannic acid, α-borneol, tocopherol nicotinate, inositol hexanicotinate, cyclane derrate, Cinnarizine, tolazoline, acetylcholine, Verapamil, cepharanthine and γ-oryzanol; antiseborrhoeic agents such as sulfur and thianthol; tranexamic acid, thiotaurine and hypotaurine.

Thus, the fine particle dispersant of the present invention contributes to the stable dispersion of fine particles for a relatively long period of time in the field of the dispersion in which fine particles are to be dispersed. This dispersant is expected to be effective in the production and storage of the above-described products.

The amount of the fine particle dispersant of the present invention to be added to the cosmetics, paints, inks, memorizing materials, lubricants, etc. is to be determined depending on the kind and amount of the fine particles to be dispersed. This dispersant is generally incorporated in an amount of preferably at least about 5% by mass, more preferably at least 15% by mass, into the composition of cosmetics, paints, inks, memorizing agents, lubricants, etc. Concretely, the amount of the dispersant is preferably 5 to 90% by mass, more preferably 15 to 90% by mass.

The present invention provides the fine particle dispersant excellent in the fine particle dispersibility and having a high heat stability, no smell and only a slight irritating property.

The following Examples will further specifically illustrate the present invention.

EXAMPLE 1

Preparation Of Fine Particle Dispersant Containing Partial Esters of Ditrimethylolpropane and Isostearic Acid and/or Sebacic Acid 168 g (0.8 mol) of ditrimethylolpropane [ditrimethylolpropane of Koei Kagaku Co.], 392 g (1.3 mols) of isostearic acid [PRISORINE 3505 of Unichema International] and 41 g (0.2 mol) of sebacic acid [Kokura Synthetic Industries, Ltd.] were fed into a 1 L four-necked flask provided with a stirrer, thermometer, nitrogen gas inlet tube and water separating tube. Xylol was also added thereto as a reflux solvent in an amount of 5% based on the whole amount of them. The obtained mixture was stirred at 200 to 250° C. for 6 hours to carry out the reaction. After the completion of the reaction, the reaction mixture was decolored with activated clay and then deodorized by an ordinary method to obtain 436 g of partial esters of ditrimethylolpropane and isostearic acid and/or sebacic acid. The hydroxyl value (OHV) of the condensate was 92.

EXAMPLE 2

Preparation of Fine Particle Dispersant Containing Partial Esters of Ditrimethylolpropane and Isooctylic Acid 211 g (0.8 mol) of ditrimethylolpropane [ditrimethylolpropane of Koei Kagaku Co.] and 389 g (2.7 mols) of isooctylic acid [isooctylic acid or Chisso Corporation] were fed into a 1 L four-necked flask provided with a stirrer, thermometer, nitrogen gas inlet tube and water separating tube. Xylol was also added thereto as a reflux solvent in an amount of 5% based on the whole amount of them. The obtained mixture was stirred at 200 to 250° C. for 19 hours to carry out the reaction. After the completion of the reaction, the reaction mixture was decolored with activated clay and then deodorized by an ordinary method to obtain 421 g of partial esters of ditrimethylolpropane and isooctylic acid. OHV of the esterification product was 89.

EXAMPLE 3

Preparation of Fine Particle Dispersant Containing Partial Esters of Ditrimethylolpropane and Isostearic Acid 133 g (0.5 mol) of ditrimethylolpropane [ditrimethylolpropane of Koei Kagaku Co.] and 467 g (1.6 mols) of isostearic acid [PRISORINE 3505 of Unichema International] were fed into a 1 L four-necked flask provided with a stirrer, thermometer, nitrogen gas inlet tube and water separating tube. Xylol was also added thereto as a reflux solvent in an amount of 5% based on the whole amount of them. The obtained mixture was stirred at 200 to 250° C. for 5 hours to carry out the reaction. After the completion of the reaction, the reaction mixture was decolored with activated clay and then deodorized by an ordinary method to obtain 433 g of partial esters of ditrimethylolpropane and isostearic acid. OHV of the esterification product was 49.

EXAMPLE 4

Preparation Of Fine Particle Dispersant Containing Partial Esters of Ditrimethylolpropane and Isotridecanoic Acid 168 g (0.7 mol) of ditrimethylolpropane [ditrimethylolpropane of Koei Kagaku Co.] and 432 g (2.0 mols) of isotridecanoic acid [isotridecanoic acid of Nissan Chemical Industries, Ltd.] were fed into a 1 L four-necked flask provided with a stirrer, thermometer, nitrogen gas inlet tube and water separating tube. Xylol was also added thereto as a reflux solvent in an amount of 5% based on the whole amount of them. The obtained mixture was stirred at 200 to 250° C. for 9 hours to carry out the reaction. After the completion of the reaction, the reaction mixture was decolored with activated clay and then deodorized by an ordinary method to obtain 386 g of partial esters of ditrimethylolpropane and isotridecanoic acid. OHV of the esterification product was 68.

The fine particle dispersibility and thermal stability of the esterification product and the condensate thereof thus obtained as the fine particle dispersant were determined by methods described below.

EXAMPLE 5

Preparation of Fine Particle Dispersant Containing Partial Esters of Ditrimethylolpropane and Isononanoic Acid 207 g (0.8 mol) of ditrimethylolpropane [ditrimethylolpropane of Koei Kagaku Co.] and 393 g (2.5 mols) of isononanoic acid [KYOWANOIC-N of Kyowa Hakko Kogyo Co., Ltd.] were fed into a 1 L four-necked flask provided with a stirrer, thermometer, nitrogen gas inlet tube and water separating tube. Xylol was also added thereto as a reflux solvent in an amount of 5% based on the whole amount of them. The obtained mixture was stirred at 200 to 250° C. for 11 hours to carry out the reaction. After the completion of the reaction, the reaction mixture was decolored with activated clay and then deodorized by an ordinary method to obtain 430 g of partial esters of ditrimethylolpropane and isononanoic acid. OHV of the esterification product was 84.

Pigment Dispersibility Test

Production of Pigment Preparation 60 g of the fine particle dispersant obtained in any of Examples 1 to 5 or castor oil in Comparative Example 1 and 40 g of a red pigment (Red No. 202 SG of Kishi Kasei, Ltd.) were premixed together in a 200 ml glass beaker. Then the obtained mixture was homogeneously kneaded with a triple-roll mill for about 10 minutes to obtain a pigment preparation.

Determination of Dispersibility 25 g of the pigment preparation produced as described above was weighed and fed into a 200 ml stainless steel mug. 75 g of a diluting oil (liquid paraffin, T.I.O: glyceryl tri-2-ethylhexanoate) was poured therein, and they were stirred with a homomixer provided with Disper mill at 1000 rpm for 5 minutes. 20 ml of the preparation thus thoroughly mixed with the homomixer was poured into lidded 20 ml test tube. The lidded test tube containing the preparation was left to stand in a constant temperature bath at 40° C. for 3 days and then the sedimentation rate in each test tube was determined.

The expression "sedimentation rate" herein indicates the degree of the sedimentation, namely, the distance of the pigment dispersion layer (layer colored in red) from the surface of the pigment dispersion originally poured into the test tube. The sedimentation rate is expressed by a percentage as calculated according to the following formula:

Sedimentation rate=(distance of the upper layer separated from the prepared dispersion)/(height of the poured pigment dispersion).

The lower the rate, the higher the dispersibility.

The obtained sedimentation rates are shown in Table 1.

TABLE 1

| Oil | Sedimentation rate after leaving in constant temp. bath at 40° C. for 3 days (%) | |
| --- | --- | --- |
|  | Liquid paraffin | T.I.O |
| Example 1 | 1 | 1 |
| Example 2 | 18 | 0 |
| Example 3 | 20 | 3 |
| Example 4 | 22 | 2 |
| Example 5 | 19 | 3 |
| Comp. Ex. 1 | —* | 5 |

—*: When castor oil of Comparative Example 1 was used as the dispersant and liquid paraffin was used as the diluting oil, the test could not be carried out because the homogeneous mixing of the pigment preparation with the liquid paraffin was impossible. On the contrary, the fine particle dispersant of the present invention had an excellent dispersing effect.

Thermal Stability Test

Air was blown into samples and the samples were continuously heated at a predetermined temperature to determine the deterioration of the samples with time. Concretely, the thermal stability tests were carried out at 120° C. for 48 hours with Rancimat type 743 (an automatic oil and fat stability tester of Metrohm), and the deterioration in the properties (smell and color) of each sample was compared with that of castor oil (Comparative Example 1). The results were shown according to the following standards:

Smell:
 ◯: superior
 Δ: equivalent
 X: inferior
Color:
 ⊚: unchanged
 ◯: slightly colored
 Δ: equivalent
 X: inferior The results thus obtained are shown in Table 2.

TABLE 2

| | Thermal stability | |
| --- | --- | --- |
| | Properties after 48 hours | |
| | Smell | Color |
| Example 1 | ◯ | ◯ |
| Example 2 | ◯ | ⊚ |
| Example 3 | Δ | ◯ |

TABLE 2-continued

Thermal stability

| | Properties after 48 hours | |
|---|---|---|
| | Smell | Color |
| Example 4 | Δ | ○ |
| Example 5 | Δ | ○ |
| Comp. Ex. 1 | Δ | Δ |

EXAMPLE 5

Preparation of Lipsticks 74 g of the fine particle dispersant obtained in Example 1 or 2 or castor oil in Comparative Example 1, 10 g of one of the pigments obtained in the above-described pigment dispersibility tests, 8 g of candelilla wax and 8 g of ceresine wax were heated to around 90° C., and the obtained melt was homogeneously mixed. The homogeneous mixture thus obtained was defoamed and then cast to fill a mold for forming lipsticks. After cooling, lipsticks were obtained.

Evaluation of Properties of Lipsticks

The gloss and breaking resistance of the lipsticks and the feeling realized by the use of them (spreadability and close adherence to the lips) were evaluated and compared with each other.

As for the gloss, the lipsticks thus prepared were flamed and then the degrees of the gloss of the flamed surfaces thereof were compared with one another. The results equivalent to those in Comparative Example 1 were shown by ○ and those superior to those in Comparative Example 1 were shown by ⊚. In cutting tests with a piano wire, the results were determined with Rheometer NRM-2002J (a product of Fudoh Kougyou, Ltd., and the results equivalent to those in Comparative Example 1 were shown by ○ and those superior to those in Comparative Example 1 were shown by ⊚.

As for the feeling realized after the use of the lipsticks, 10 panelists evaluated the spreadability and adherence of them after using the lipsticks. The results equivalent to those in Comparative Example 1 were shown by ○ and those superior to those in Comparative Example 1 were shown by ⊚.

TABLE 3

Evaluation of properties of lipsticks

| | | Cutting test | Feeling after use | |
|---|---|---|---|---|
| | Gloss | with piano wire | Elongation | Adhesion |
| Fine particle dispersant-containing lipstick in Example 1 | ⊚ | ⊚ | ○ | ⊚ |
| Fine particle dispersant-containing lipstick in Example 2 | ⊚ | ○ | ⊚ | ○ |
| Fine particle dispersant-containing lipstick in Comp. Ex. 1 | ○ | ○ | ○ | ○ |

What is claimed is:

1. A cosmetic composition comprising a fine particle dispersant,
said fine particle dispersant containing at least one member selected from the group consisting of:
(i) polycondensates of ditrimethylolpropane and a polyvalent carboxylic acid(s),
(ii) polycondensates of an ester compound of the following general formula (I) of ditrimethylolpropane and a fatty acid(s) and the polyvalent carboxylic acid(s)

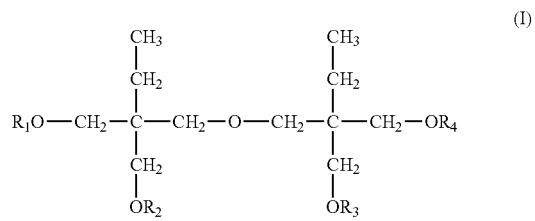

wherein $R_1$ to $R_4$ each independently represent a hydrogen atom or a fatty acid residue, with the proviso that at least one of them is a hydrogen atom and the polycondensates have hydroxoryl value of 10 to 150,
(iii) polycondensates of an ester compound of ditrimethylolpropane and the polyvalent carboxylic acid(s) and the fatty acid(s), and
(iv) polycondensates of ditrimethylolpropane, the fatty acid(s) and the polyvalent carboxylic acid(s).

2. The cosmetic composition of claim 1, wherein the polyvalent carboxylic acid(s) is a dibasic acid(s).

3. The cosmetic composition of claim 1, wherein the fatty acid(s) is isostearic acid and the polyvalent carboxylic acid(s) is sebacic acid.

4. The cosmetic composition of claim 1, wherein the fatty acid(s) is a branched saturated fatty acid(s) having 8 to 18 carbon atoms.

5. The cosmetic composition of claim 1, wherein the molar ratio of the fatty acid(s) to the polyvalent carboxylic acid(s) is 70/30 to 95/5.

6. The cosmetic composition of claim 1, wherein the fine particle dispersant which contains a polycondensate of ditrimethylolpropane, a fatty acid(s) and a polyvalent carboxylic acid(s), wherein the fatty acid(s) is a branched fatty acid(s) having 8 to 18 carbon atoms, the polyvalent carboxylic acid(s) is a dibasic carboxylic acid(s) having 2 to 10 carbon atoms and the polycondensate has a hydroxyl value of 40 to 100.

* * * * *